(12) United States Patent
Tanifuji

(10) Patent No.: US 6,941,238 B2
(45) Date of Patent: Sep. 6, 2005

(54) MEASUREMENT DEVICE AND DATA DISPLAYING METHOD

(75) Inventor: Norio Tanifuji, Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 10/753,641

(22) Filed: Jan. 8, 2004

(65) Prior Publication Data
US 2004/0173026 A1 Sep. 9, 2004

(30) Foreign Application Priority Data
Jan. 9, 2003 (JP) .................................. 2003-002810

(51) Int. Cl.[7] .......................... G01L 15/00; G06F 11/30
(52) U.S. Cl. .................... 702/127; 702/139; 702/176; 702/188
(58) Field of Search ............................ 702/127, 139, 702/176, 178, 187, 188; 600/485, 490, 500, 503, 595

(56) References Cited

U.S. PATENT DOCUMENTS 5,795,301 A * 8/1998 Yasukawa et al. .......... 600/500
5,941,837 A * 8/1999 Amano et al. ............. 600/595

* cited by examiner

*Primary Examiner*—Bryan Bui
(74) *Attorney, Agent, or Firm*—Adams & Wilks

(57) ABSTRACT

A measurement device for measuring and displaying a physical quantity such as a heartbeat, an atmospheric pressure or temperature, or the like, includes a clock for counting time, a physical quantity measuring device for measuring the physical quantity to be displayed, a processor for determining a plurality of values based on the measured physical quantity and the counted time, a first display for simultaneously displaying the plurality of values and a second display for magnifying at least one of the values and displaying the magnified value.

18 Claims, 16 Drawing Sheets

MEASUREMENT DEVICE AND DATA DISPLAYING METHOD

BACKGROUND OF THE INVENTION

1. Field of the Invention

The present invention relates to a measurement device for measuring and displaying a physical quantity such as a heartbeat, a pulsation, an atmospheric pressure, or an atmospheric temperature.

2. Description of the Prior Art

Biological information such as a heartbeat or a pulsation, and environmental information such as an atmospheric pressure or an atmospheric temperature are sometimes measured during sports training, such as running. Since it is desirable for a user (e.g. a runner) to be able to timely check the measurement results, a measurement device desirably has a wearable construction. In addition, since the measurement device should not interfere with running, the measurement device needs to be miniature and light. Measurement devices which meet these requests include measurement devices integrated with a watch, and a watch type measurement device.

A display area is extremely limited due to the request for miniaturization. However, it is desirable that the display of the measurement device is easy to see so that the user himself/herself can check the measurement results during training. There is a measurement device for displaying the measurement results in the form of a graph in order to make its display easy to see (refer to JP 10-234685 A, for example).

The measurement device described in JP 10-234685A is adapted to process the measured biological information in accordance with a processing mode set by a user to display the processing results on a segmented display unit or a dot matrix display unit. The segmented display unit is a display unit capable of displaying numeric values to display thereon accurate values concerned with the processing results. The dot matrix display unit displays thereon the processing results in the form of a graph, such as a bar graph, which the user can easily check at a glance, on the basis of a combination of displays of the coordinates represented by the corresponding values on the X-axis and the y-axis.

It is considered to be desirable that as a scale of the x-axis and the y-axis, a maximum scale with which the processing results can be displayed within a screen is automatically selected so that the user can easily check a change in data. In addition, as for information displayed by such a measurement device, various kinds of information are conceivable. It is possible to display a target range set by the user together with a graph of a mean value or an instantaneous value.

For a measurement device of this sort, there are a large number of items that the user wants to be displayed, including a physical quantity such as a heartbeat, a pulsation, an atmospheric temperature, and an atmospheric pressure, a relationship between a physical value and a target value, a graph representing a change in physical quantity, a count value of a time, and a lap value. If all of these items are intended to be simultaneously displayed on a screen, it is necessary to display each item in a small size, or to increase the size of the screen.

If each item is displayed in a small size, it is difficult for the user to check the item. On the other hand, it is not preferable to increase the size of the screen because a measurement device is preferably small and light.

SUMMARY OF THE INVENTION

An object of the present invention is to provide a measurement device which is capable of displaying a large number of items of information, and allows a user to readily check information.

In order to achieve the above-mentioned object, a measurement device according to the present invention includes:

physical quantity measurement means for measuring a physical quantity;

time measurement means for counting a time;

calculation processing means for receiving as an input, the physical quantity measured by the physical quantity measurement means and the time counted by the time measurement means to execute processing to calculate a plurality of items;

first display means for simultaneously displaying thereon the plurality of items; and second display means for magnifying at least one item selected from the plurality of items and displaying thereon the magnified item.

Consequently, according to the measurement device of the present invention, the plurality of items are displayed on the first display means, and any of the items is magnified (enlarged) and displayed on the second display means. As a result, a plurality of kinds of data can be checked, and also the data of the specific item can be more readily checked.

Further, the measurement device according to the present invention may further include display control means for controlling the second display means to magnify the selected item to display thereon the selected item when the selected item meets a predetermined condition.

Consequently, the plurality of items are displayed on the first display means, and the items meeting the predetermined condition are automatically magnified and displayed on the second display means. As a result, a plurality of kinds of data can be checked, and the data involving a change can be readily checked as well.

Also, it is possible that the display control means, when the data of any one of the items is updated, judges that the predetermined condition is met, and controls the second display means so as to magnify the data of the item to display thereon the updated item.

Also, the measurement device according to the present invention may further include switch input means for detecting a manipulation of a switch, in which when any one of the items is selected on the basis of the manipulation of the switch input means, the display control means controls the second display means so as to magnify the data of the item to display the data of the item.

Consequently, the data of a plurality of items is displayed on the first display means, and the data of the items selected by a user is magnified and displayed on the second display means. As a result, the data of a plurality of items can be checked, and also the data which a user demands to check can be more readily checked.

Also, it is possible that the physical quantity includes at least one of a heart rate, a pulse rate, an atmospheric pressure, and an atmospheric temperature.

Also, it is possible that the items include at least a ratio of a physical quantity to a preset target value.

Consequently, since the ratio of the measured physical quantity to the target value of the physical quantity is displayed, it is possible to readily grasp a relationship between the measured physical quantity and the target value.

Also, it is possible that a display of the first display means is semitransmissive, the first display means and the second display means are provided so as to overlap each other with the second display means being provided on a side of a line of sight, and the display of the first display means is transmitted through the second display means to be visually recognized.

Consequently, the data of a plurality of items displayed on the first display means can be visually recognized, and the data magnified and displayed on the second display means can be readily visually recognized as well.

A measurement device according to another aspect of the present invention includes:

physical quantity measurement means for measuring a physical quantity;

calculation processing means for calculating a ratio of the physical quantity measured by the physical quantity measurement means to a preset target value; and display means for displaying thereon the ratio.

A data displaying method according to the present invention which is used for a measurement device having a first display means for simultaneously displaying thereon data of a plurality of items, and a second display means for magnifying any one of the items to display thereon the magnified item, and serves to display the data of the plurality of items on the basis of a measured physical quantity, includes:

A step of continuously displaying the data of the plurality of items on the first display means; and a step of magnifying and displaying the data of the item that meets a predetermined condition, of the data of the plurality of items on the second display means.

A data displaying method according to another aspect of the present invention, which is used for a measurement device having a first display means for simultaneously displaying thereon data of a plurality of items, and a second display means for magnifying any one of the items to display thereon the magnified item, and serves to display the data of the plurality of items on the basis of a measured physical quantity, includes:

A step of continuously displaying the data of the plurality of items on the first display means; and a step of magnifying and displaying the data of the item, selected on the basis of a switch input, of the data of the plurality of items on the second display means.

BRIEF DESCRIPTION OF THE SEVERAL VIEWS OF THE DRAWINGS

A preferred form of the present invention is illustrated in the accompanying drawings in which.

DETAILED DESCRIPTION OF THE PREFERRED EMBODIMENTS

An embodiment mode of the present invention will hereinafter be described in detail with reference to the accompanying drawings.

Figure 1:
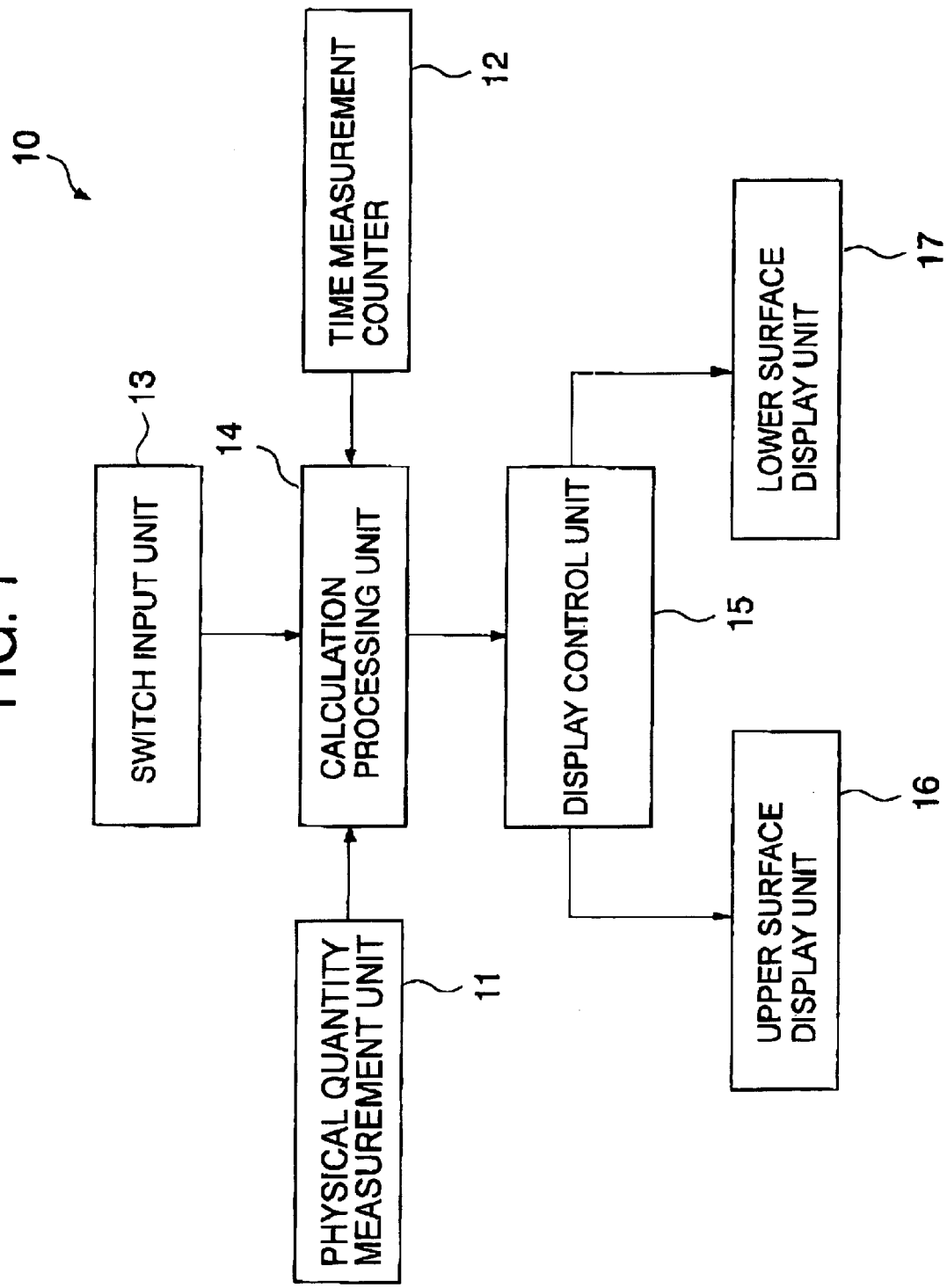
FIG. 1 is a block diagram showing a configuration of a measurement device according to an embodiment mode of the present invention.

FIG. 1 is a block diagram showing a configuration of a measurement device of this embodiment mode. Referring to FIG. 1, a measurement device 10 includes a physical quantity measurement unit 11, a time measurement counter 12, a switch input unit 13, a calculation processing unit 14, a display control unit 15, an upper surface display unit 16, and a lower surface display unit 17.

The physical quantity measurement unit 11 serves to measure a physical quantity such as a heartbeat, a pulsation, an atmospheric pressure, or an atmospheric temperature and to inform the calculation processing unit 14 of the measured physical quantity. The time measurement counter 12 serves to measure a time.

The switch input unit 13 serves to inform the calculation processing unit 14 of information input through a manipulation made by a user. For example, the information input by the user means information used to instruct the physical quantity measurement unit 11 or the time measurement counter 12 to start and stop the measurement, or information used to instruct the display control unit 15 to change the displayed contents over to other displayed contents, for example.

The calculation processing unit 14 executes various kinds of processing using the time measured by the time measurement counter 12 and a physical quantity measured by the physical quantity measurement unit 11. For example, an atmospheric temperature or an atmospheric pressure is measured at regular time intervals, and a pulse rate or a heart rate is measured at regular time intervals. The measurement results are displayed in the form of a graph. As another example, there is calculated a ratio of a physical quantity measured by the physical quantity measurement unit 11 to a preset target value of the physical quantity. In addition, as still another example, there is calculated a difference between a physical quantity and a target value of the physical quantity.

The display control unit 15 displays the processing results obtained from the calculation processing unit 14 on a display unit in accordance with information sent from the switch input unit 13. The display unit of the measurement device 10 of the present invention has a two-stage construction including the upper surface display unit 16 and the lower surface display unit 17. In addition, an upper deflecting plate 21 of the upper surface display unit 16, and an upper deflecting plate 23 of the lower surface display unit 17 are different in color from each other.

Figure 2:
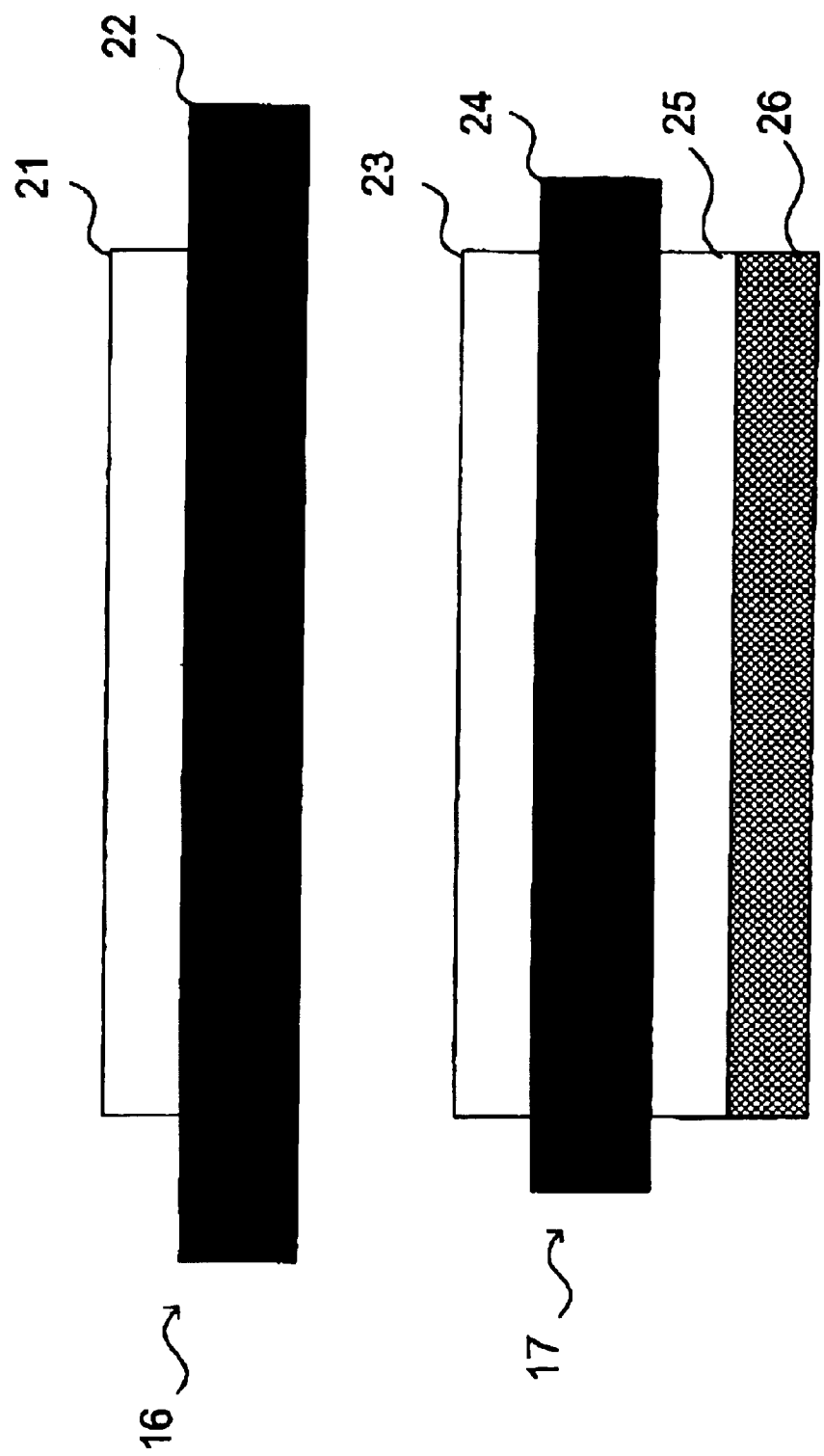
FIG. 2 is a cross-sectional view showing a structure of a display unit.

FIG. 2 is a cross-sectional view showing a structure of the display unit. Referring to FIG. 2, two liquid crystal panels, i.e., the upper surface display unit (upper panel) 16 and the lower surface display unit (lower panel) 17 overlap each other. The structure shown in FIG. 2 is obtained when viewed from an upper position of a line of sight of a user. The upper surface display unit 16 has a structure in which the upper deflecting plate 21 is provided on a liquid crystal plate 22. The lower surface display unit 17 has a structure in which a liquid crystal plate 24 is sandwiched between the upper deflecting plate 23 and the lower deflecting plate 25, and a semitransmissive reflecting plate 26 is provided so as to underlie the lower deflecting plate 25.

Both the liquid crystal plates 22 and 24 are semitransmissive liquid crystal plates. Further, no reflecting plate is provided between the liquid crystal plates 22 and 24, and the semitransmissive reflecting plate 26 is provided so as to underlie only the liquid crystal plate 24. For this reason, since the display of the liquid crystal plate 24 is transmitted through the display of the liquid crystal plate 22, when viewed from above, two displayed contents appear to overlap each other. However, the displayed contents of the liquid crystal plate 22, i.e., the displayed contents of the upper surface display unit 16 are viewed more clearly than those of the liquid crystal plate 24, i.e., those of the lower surface display unit 17.

It is supposed that the measurement device 10 of this embodiment mode is adapted to display data of items such as a target value set by a user, a physical quantity such as a measured heartbeat or pulsation, a ratio of the physical quantity to the target value of the physical quantity, a graph representing a change of the physical quantity, a count value of a time, a lap value, and a difference between the physical quantity and the target value of the physical quantity.

In the measurement device 10, a screen of the lower surface display unit 17 is divided into a plurality of areas so as to display all the items on the division areas at the same time, and any one of those items is magnified and displayed on the screen of the upper surface display unit 16.

Figure 3:
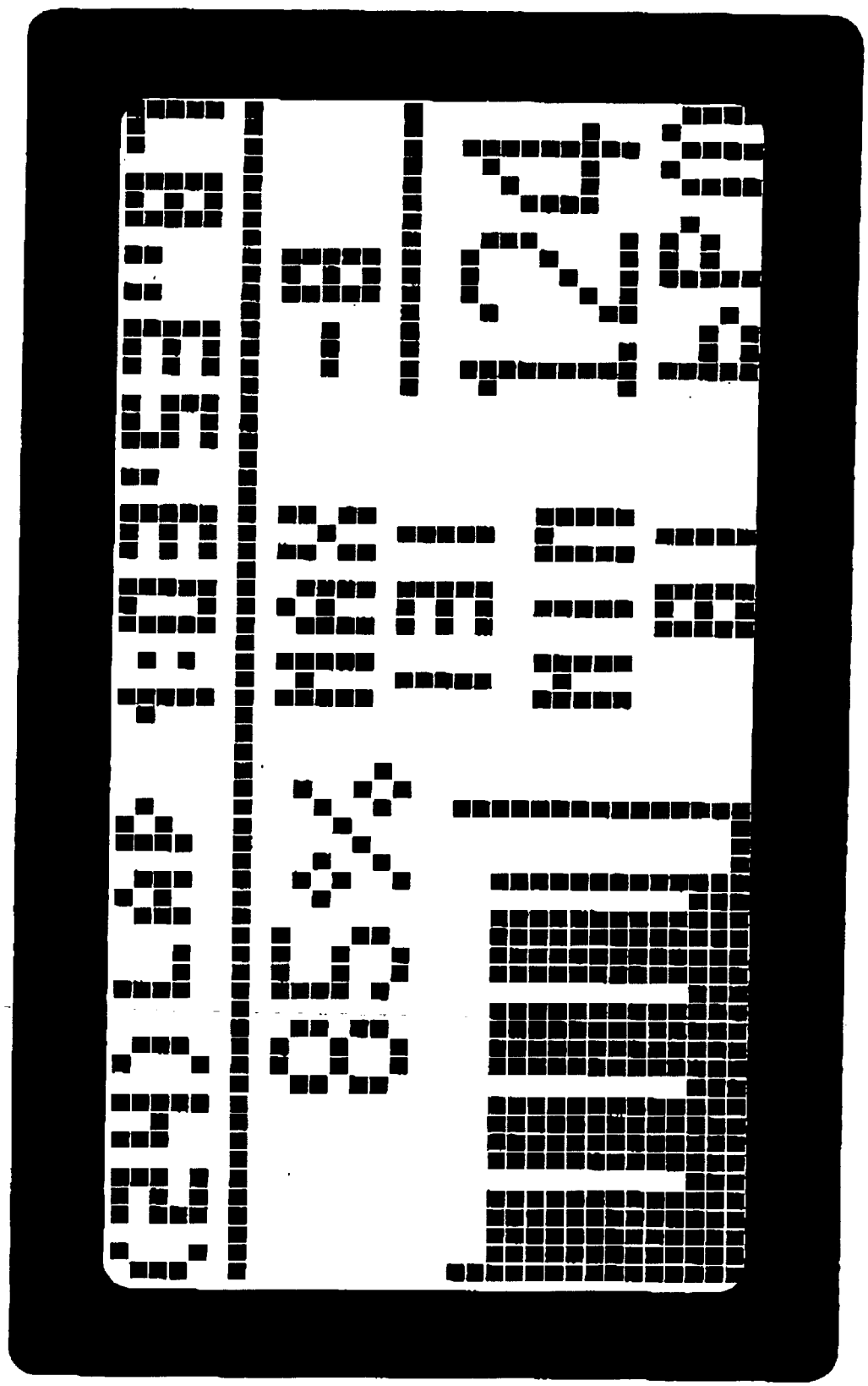
FIG. 3 is a view showing an example of displayed contents of a lower surface display unit.

FIG. 3 is a view showing an example of displayed contents on the lower surface display unit. Referring to FIG. 3, as a target value set by a user, a range of the target value "MAX131 MIN81" is shown in this case. In addition, as a physical quantity such as a measured heartbeat or pulsation, "124 bpm" is displayed in this case. In addition, as a ratio of the physical quantity to the target value, "85%" is displayed in this case. In addition, a graph representing a change of the physical quantity is displayed in the bottom left corner in this case. Also, as a count value of a time, "1:03'53"87 is displayed in this case. Also, as a lap value, "(24)LAP" is shown. Also, "−8" is displayed as a difference between the physical quantity and the target value.

The data of the items displayed on the screen of the upper surface display unit 16 can be changed on the basis of an input operation through the switch input unit 13. In addition; if the data of any of the items is changed, the item concerned is automatically displayed on the upper surface of the display unit 16.

Figure 4:
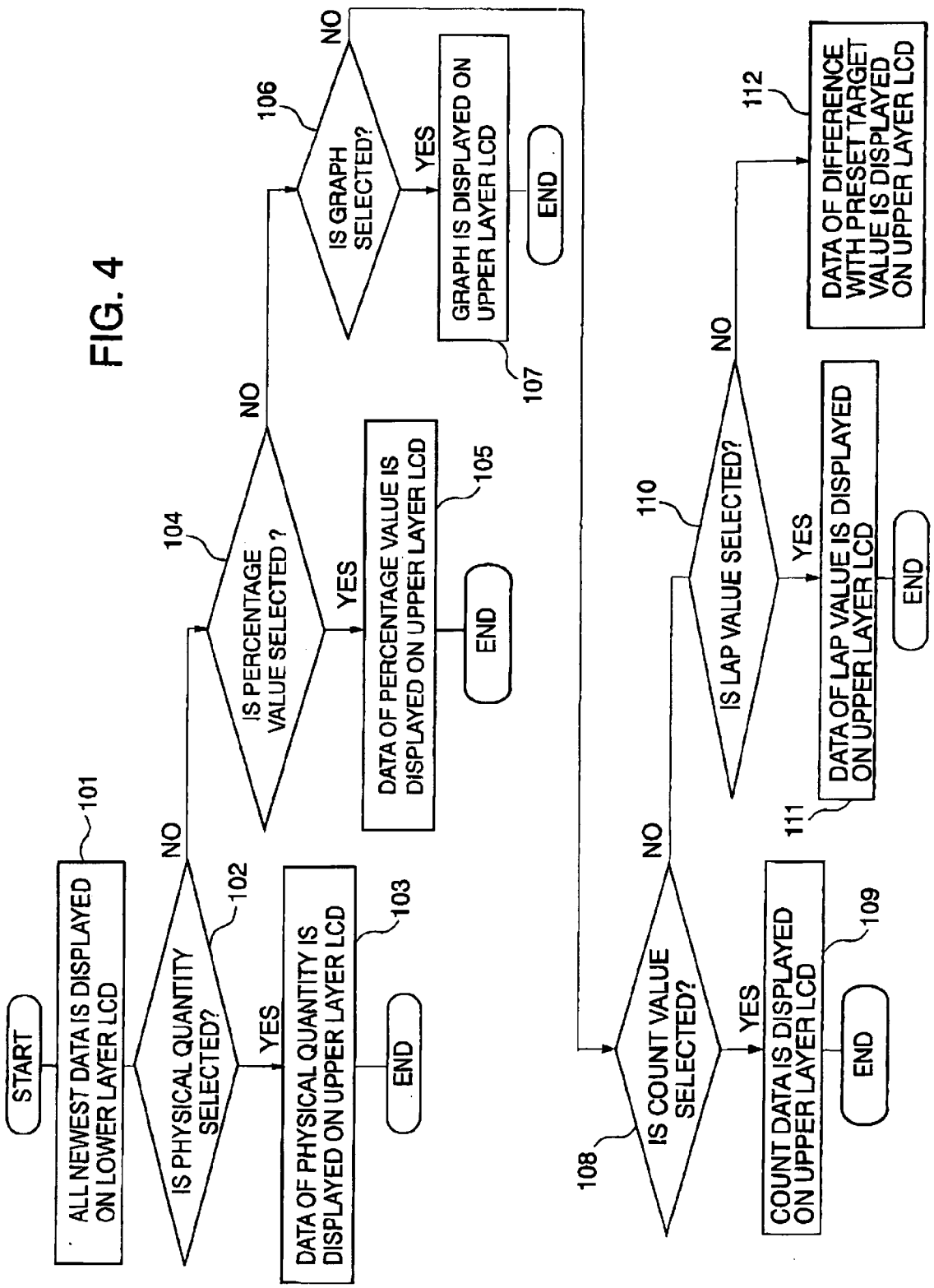
FIG. 4 is a flowchart showing an operation for changing a screen over to another screen on the basis of a switch manipulation in the measurement device according to the embodiment mode of the present invention.
Figure 5:
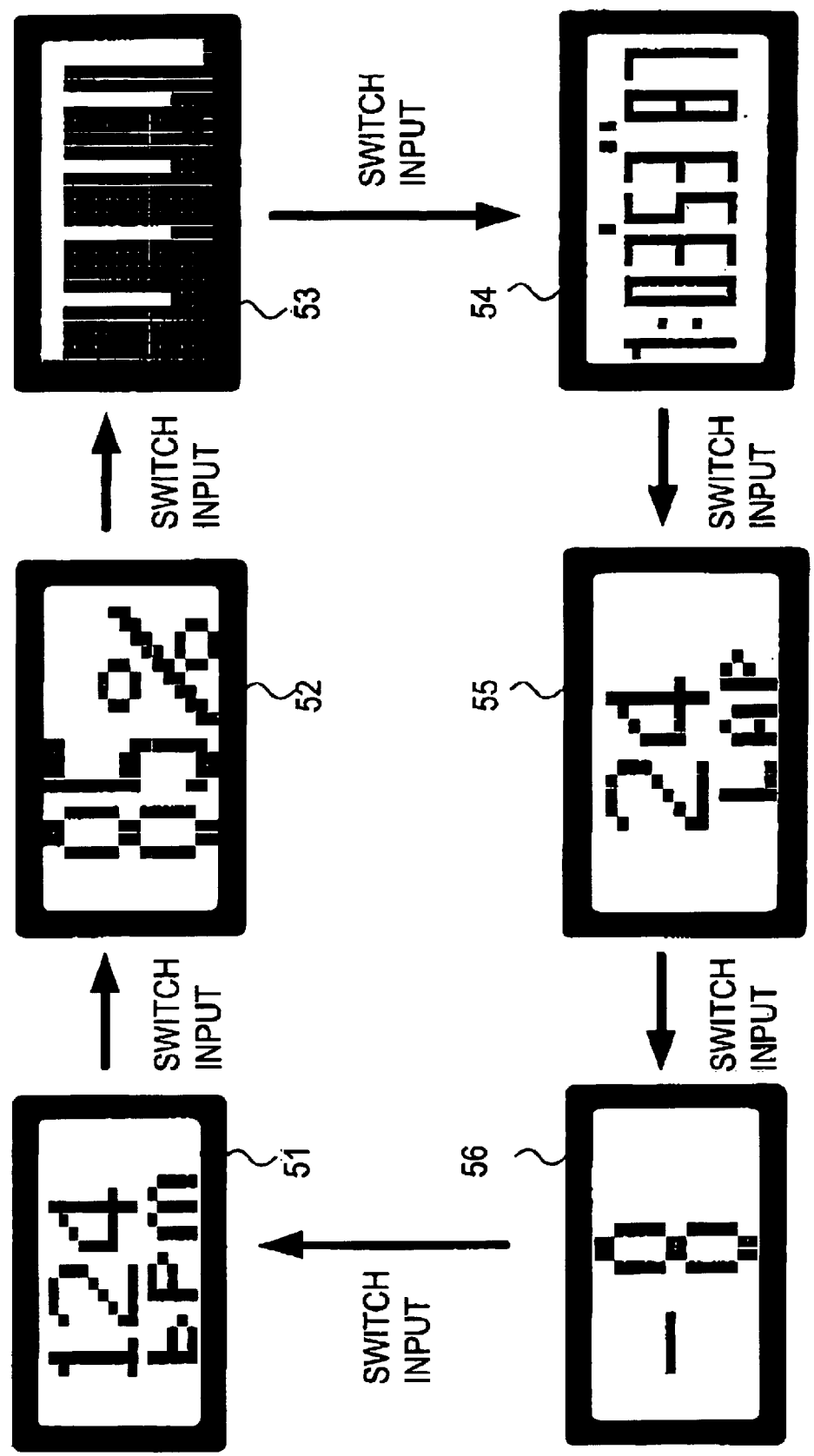
FIG. 5 is a view showing a situation of changing displayed contents of an upper surface display unit.

FIG. 4 is a flowchart showing an operation for changing a screen over to another screen on the basis of a switch manipulation in the measurement device according to this embodiment mode. FIG. 5 is a view showing a changing situation in the displayed contents of the upper surface display unit.

Referring to FIG. 4, the measurement device 10 previously displays the newest data of all the items on the lower surface display unit 17 (lower surface LCD) (Step 101).

Figure 6:
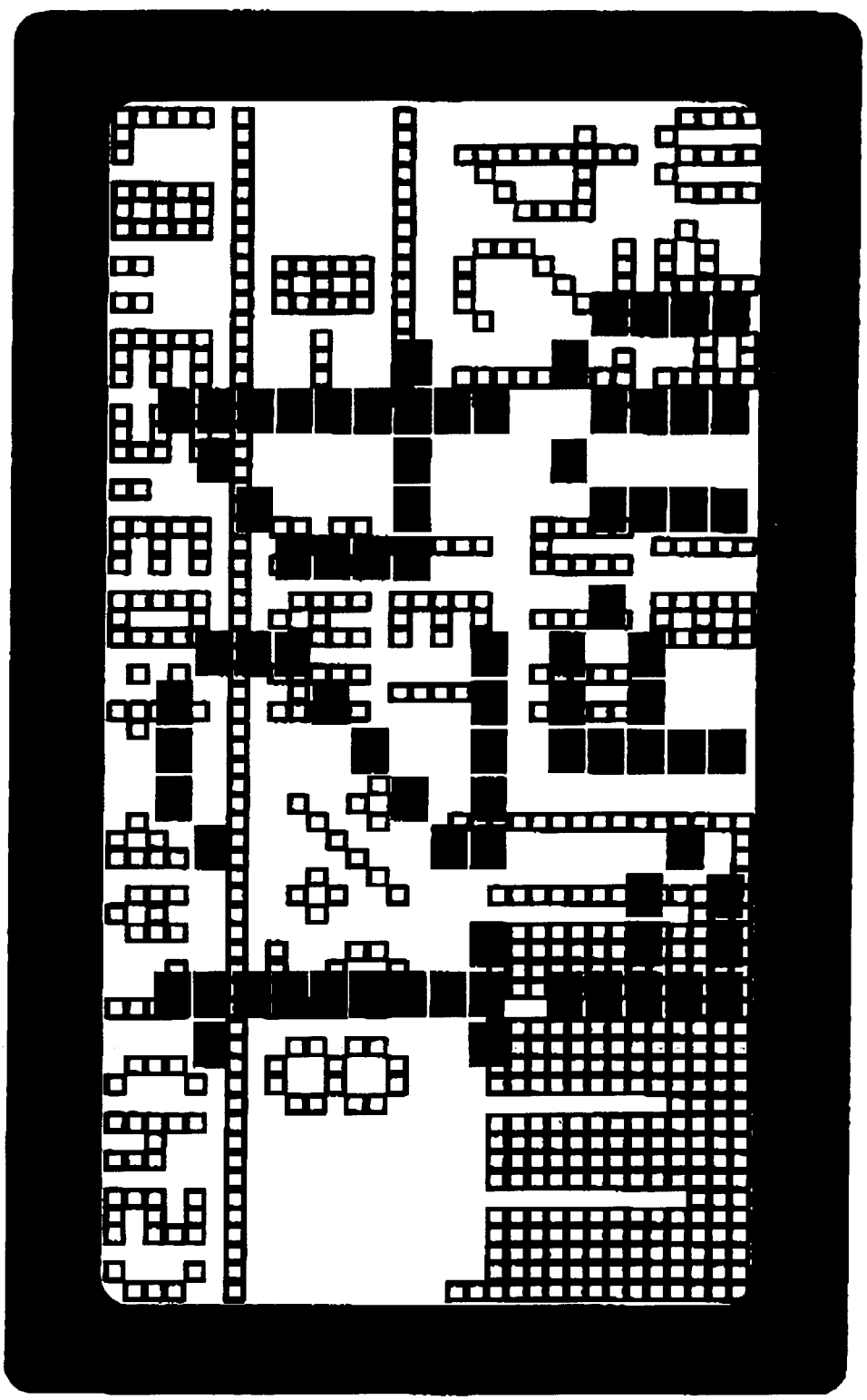
FIG. 6 is a view of a display unit as viewed from above when an item of a physical quantity is selected.

Next, the measurement device 10 judges whether or not an item of a physical quantity is selected on the basis of an input operation through the switch input unit 13 (Step 102). If an item of a physical quantity is selected, the measurement device 10 displays the data of the physical quantity on the upper surface display unit (upper layer LCD) 16 (Step 103). As a result, an image 51 shown in FIG. 5 is displayed on the upper surface display unit 16. At this time, when the display unit is viewed from above, the displayed contents of the upper surface display unit 16 and the displayed contents of the lower surface display unit 17 overlap each other to be viewed as shown in FIG. 6. In FIG. 6, the displayed contents of the upper surface display unit 16 are shown in the form of black dots, while the displayed contents of the lower surface display unit 17 are shown in the form of open dots.

Figure 7:
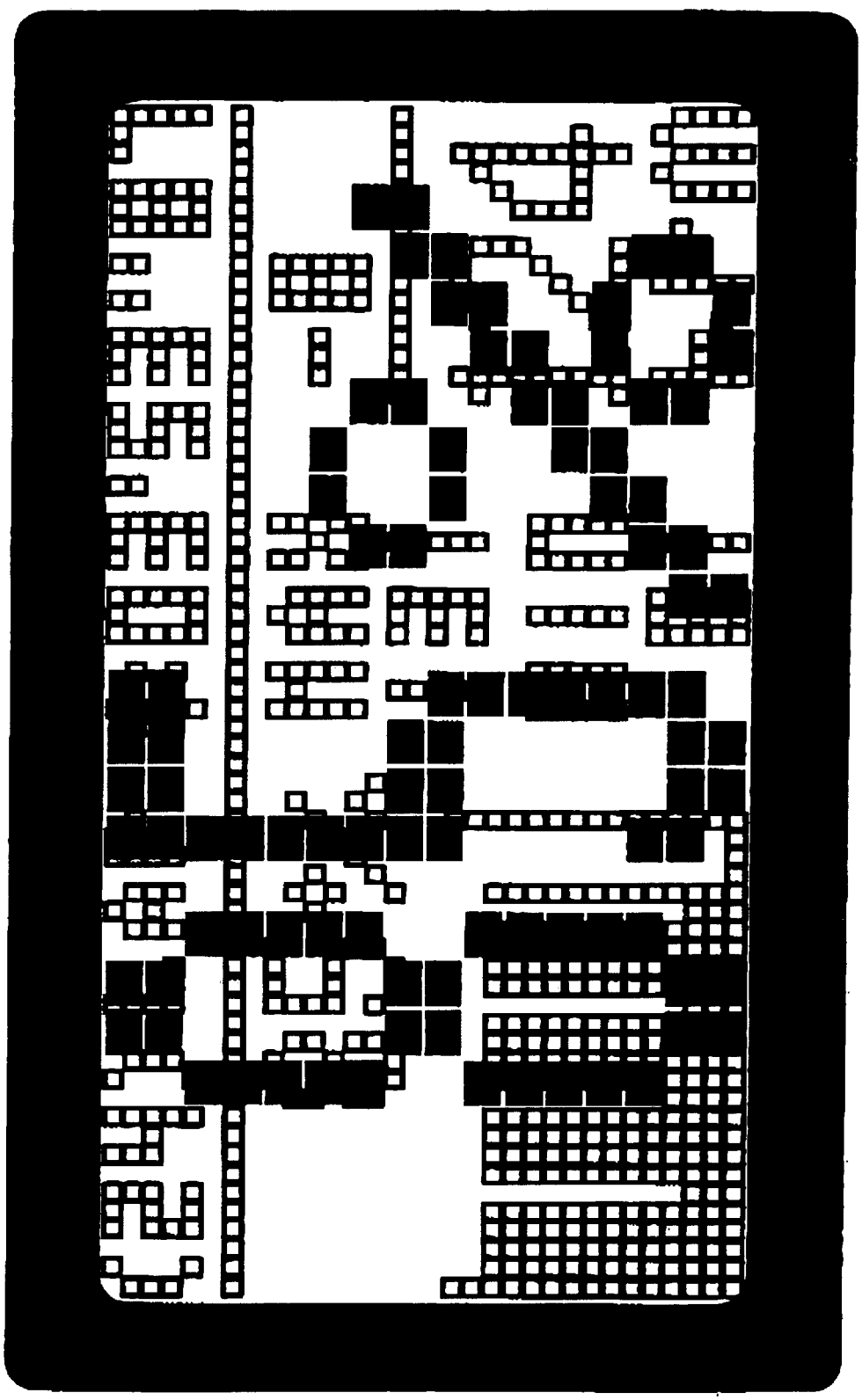
FIG. 7 is a view of the display unit as viewed from above when an item of a ratio is selected.

On the other hand, if it is judged that no item of the physical quantity is selected, the measurement device 10 next judges whether or not an item of a ratio (percentage value) of the physical quantity to a target value of the physical quantity is selected on the basis of an input operation through the switch input unit 13 (Step 104). If it is judged that the item of the percentage value is selected, then the measurement device 10 displays the data of the percentage value on the upper surface display unit 16 (Step 105). As a result, an image 52 shown in FIG. 5 is displayed on the upper surface display unit 16. At this time, when the display unit is viewed from above, the displayed contents are viewed as shown in FIG. 7.

Figure 8:
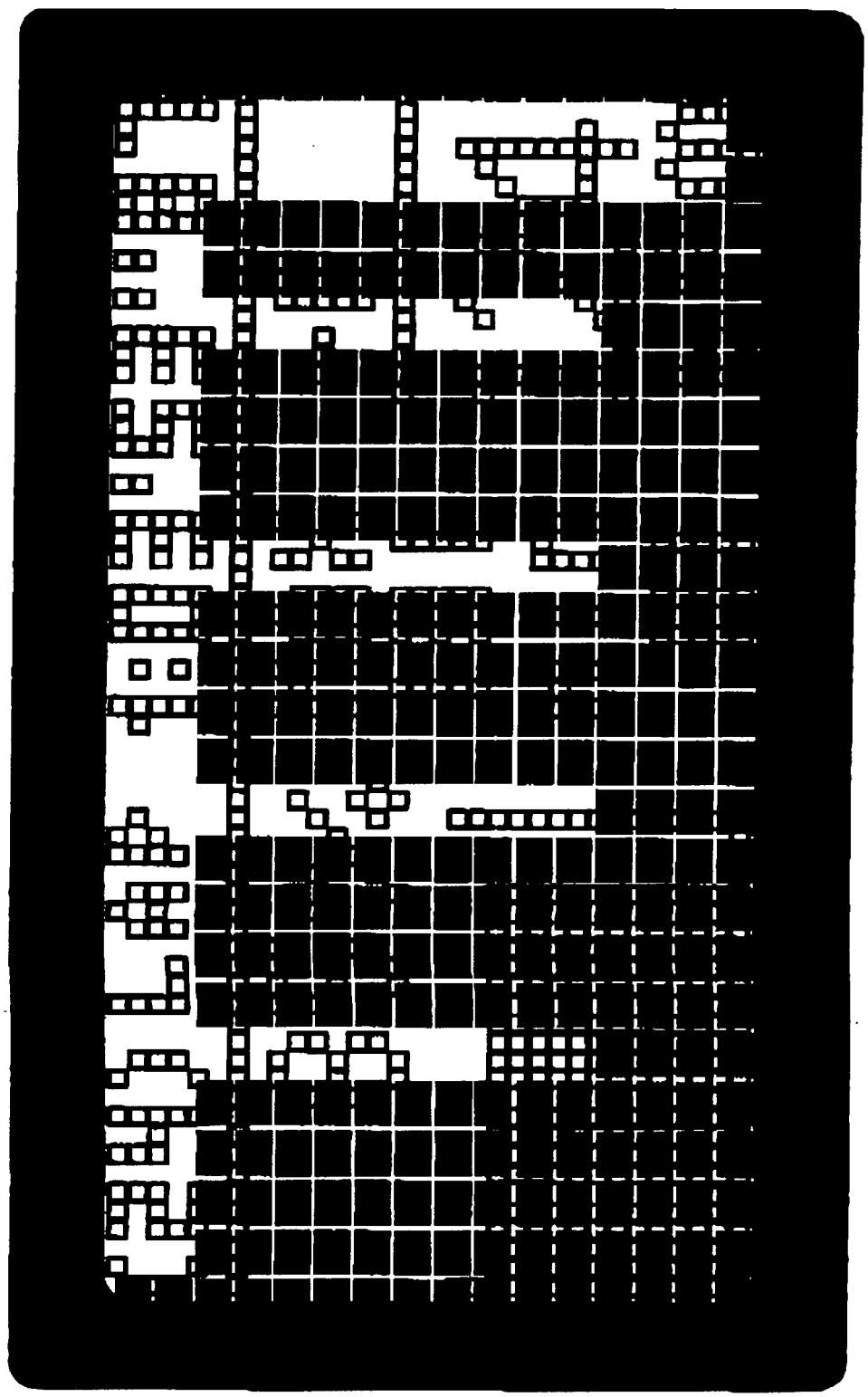
FIG. 8 is a view of the display unit as viewed from above when an item of a graph representing a change in physical quantity is selected.

On the other hand, if it is judged that the percentage value is not selected, next, the measurement device 10 judges whether or not a graph representative of a change in the physical quantity is selected on the basis of an input operation through the switch input unit 13 (Step 106). If it is judged that the graph is selected, then the measurement device 10 displays the data of the graph on the upper surface display unit 16 (Step 107). As a result, an image 53 shown in FIG. 5 is displayed on the upper surface display unit 16. At this time, when the display unit is viewed from above, the displayed contents are viewed as shown in FIG. 8.

Figure 9:
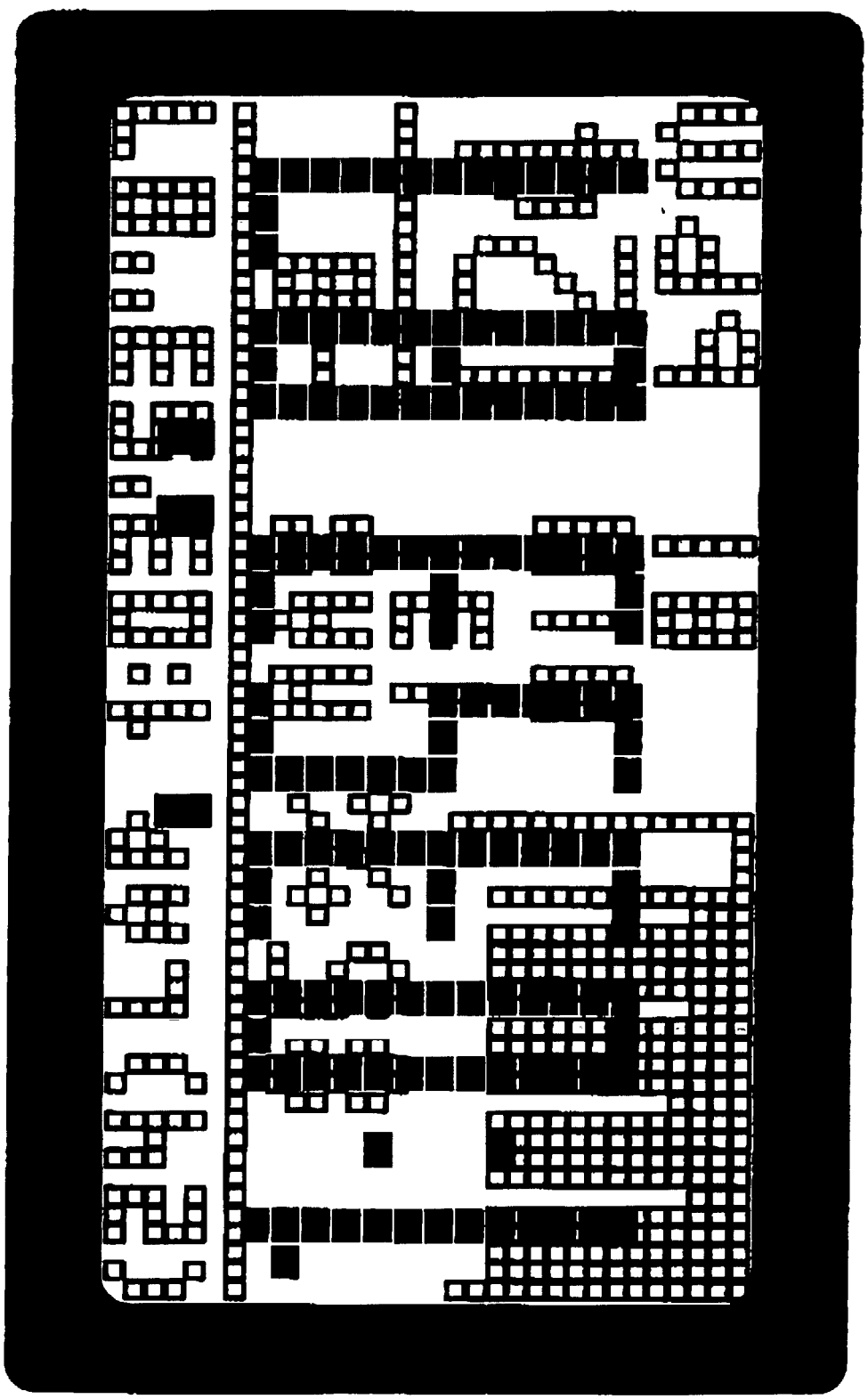
FIG. 9 is a view of the display unit as viewed from above when an item of a count value of a time is selected.

If it is judged that the graph is not selected, next, measurement device 10 judges whether or not the count value of the time is selected on the basis of an input operation through the switch input unit 13 (Step 108). If it is judged that the count value is selected, then the measurement device 10 displays the data of the count value on the upper surface display unit 16 (Step 109). As a result, an image 54 shown in FIG. 5 is displayed on the upper surface display unit 16. At this time, when the display unit is viewed from above, the displayed contents are viewed as shown in FIG. 9.

Figure 10:
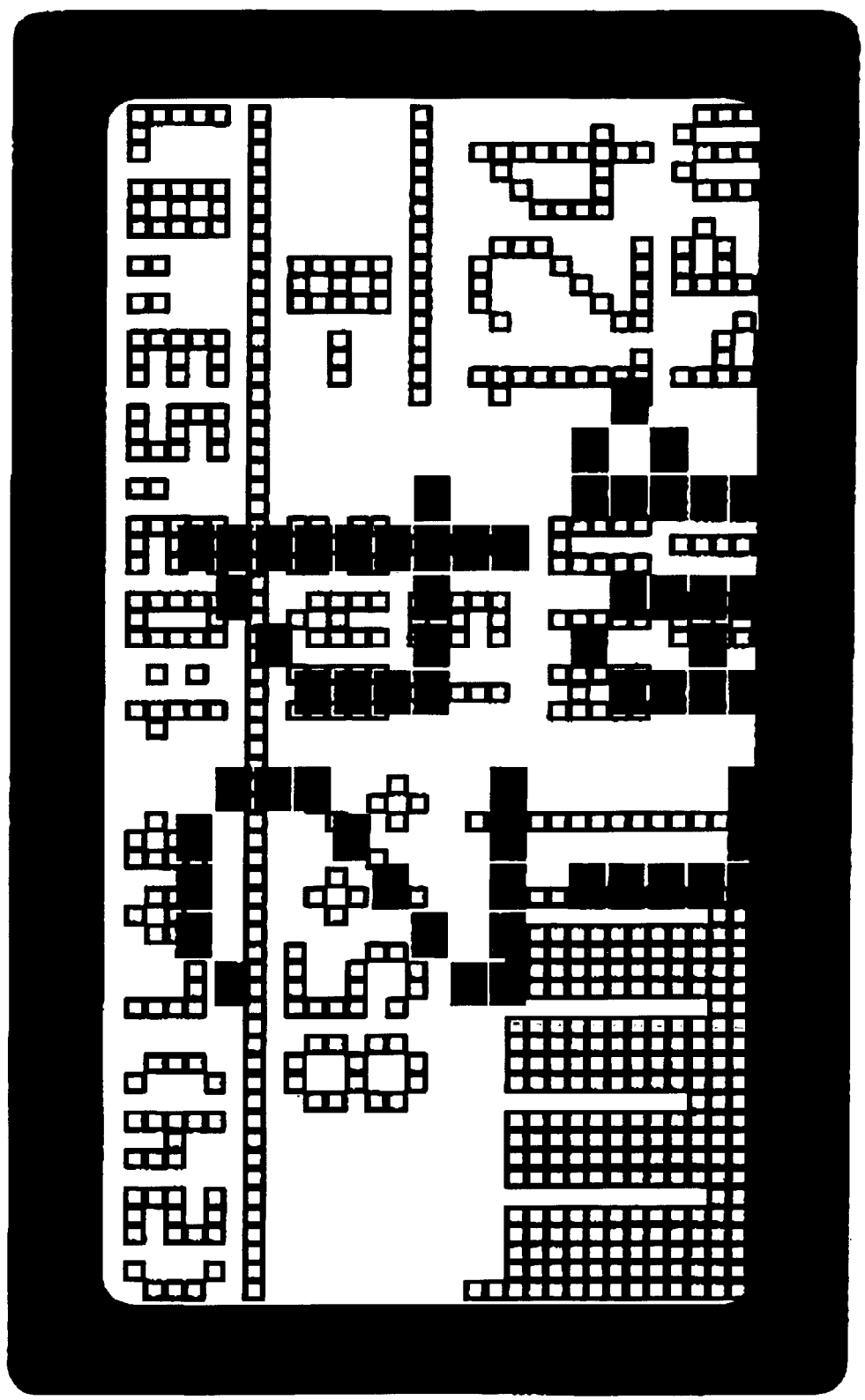
FIG. 10 is a view of the display unit as viewed from above when an item of a lap value is selected.

If it is judged that no item of the count value is selected, the measurement device 10 next judges whether or not an item of a lap value is selected on the basis of an input operation through the switch input unit 13 (Step 110). If it is judged that the item of the lap value is selected, then the measurement device 10 displays the data of the lap value on the upper surface display unit 16 (Step 111). As a result, an image 55 shown in FIG. 5 is displayed on the upper surface display unit 16. At this time, when the display unit is viewed from above, the displayed contents are viewed as shown in FIG. 10.

Figure 11:
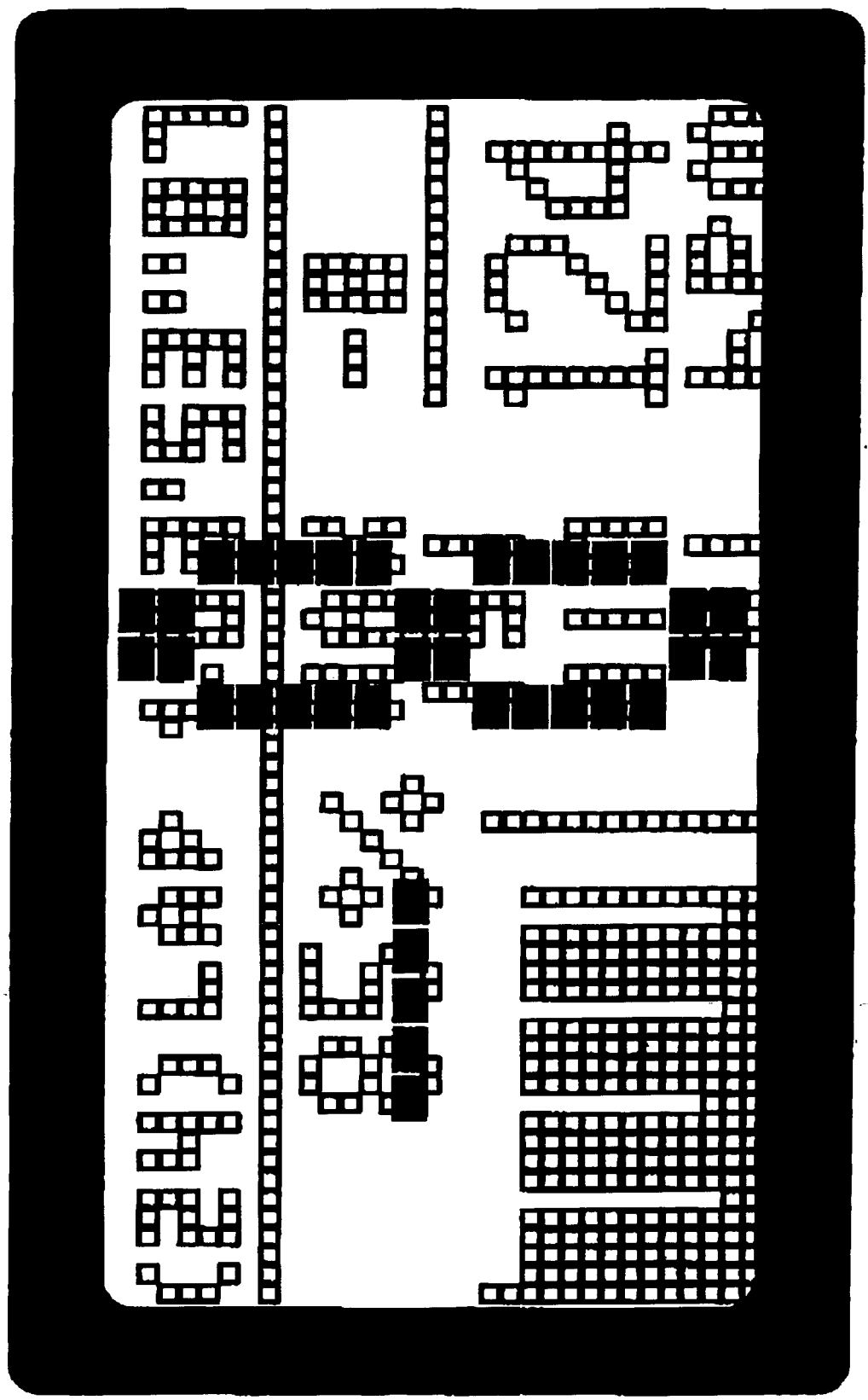
FIG. 11 is a view of the display unit as viewed from above when an item of a difference between a physical quantity and a target value of the physical quantity is selected.

On the other hand, if it is judged that no item of the lap value is selected, the measurement device 10 next displays a difference between a physical quantity and a target value of the physical quantity on the upper surface display unit 16 (Step 112). As a result, an image 56 shown in FIG. 5 is displayed on the upper surface display unit 16. At this time, when the display unit is viewed from above, the displayed contents are viewed as shown in FIG. 11.

Figure 12:
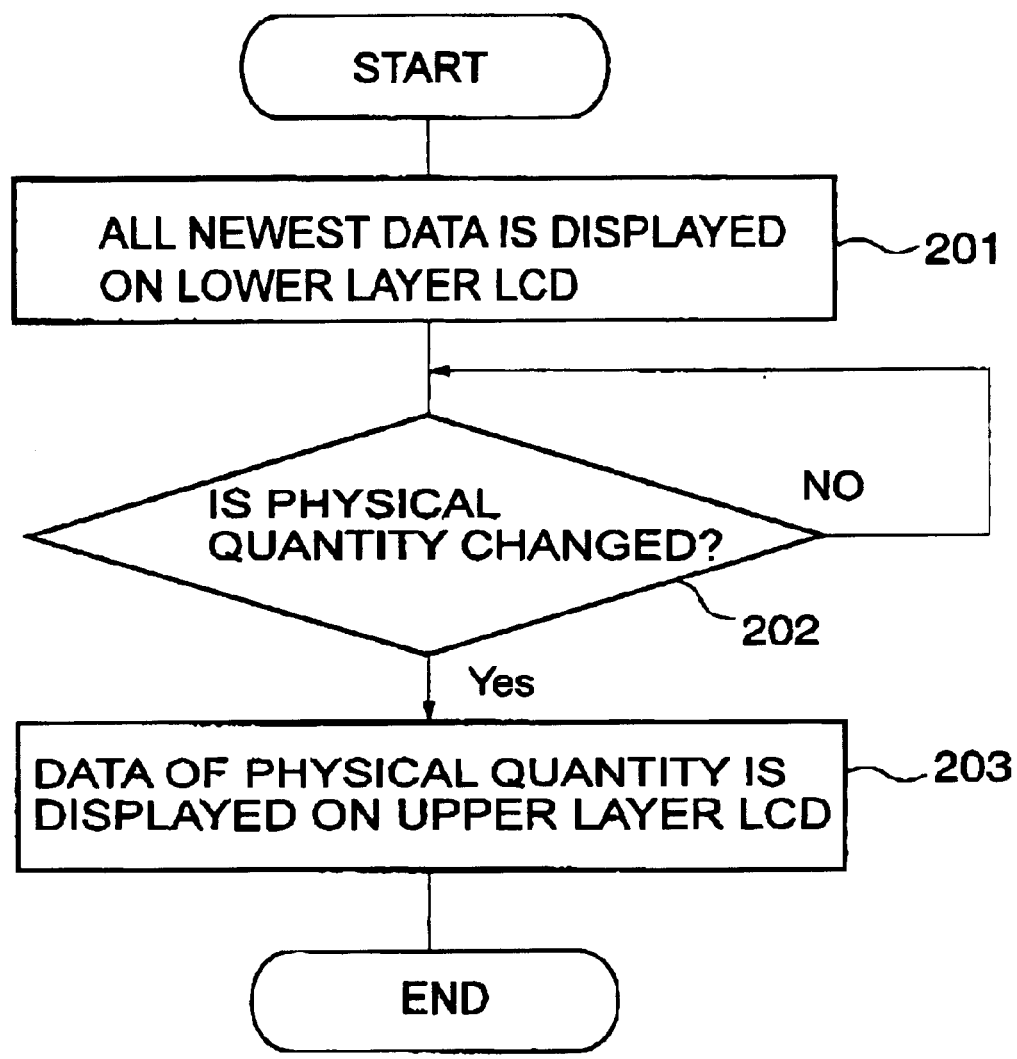
FIG. 12 is a flowchart showing an operation for changing a screen over to another screen due to a change in physical quantity in the measurement device according to the embodiment mode of the present invention.

FIG. 12 is a flowchart showing an operation for changing a screen over to another screen due to a change in physical quantity in the measurement device according to this embodiment mode. Referring to FIG. 12, the measurement device 10 previously displays the newest data of all the items on the lower surface display unit 17 (lower surface LCD) (Step 201). The measurement device 10 usually monitors a change in physical quantity (Step 202). If there is a change in physical quantity, then the measurement unit 10 displays the newest data of the physical quantity on the upper surface display unit (upper surface LCD) 16 (Step 203).

Figure 13:
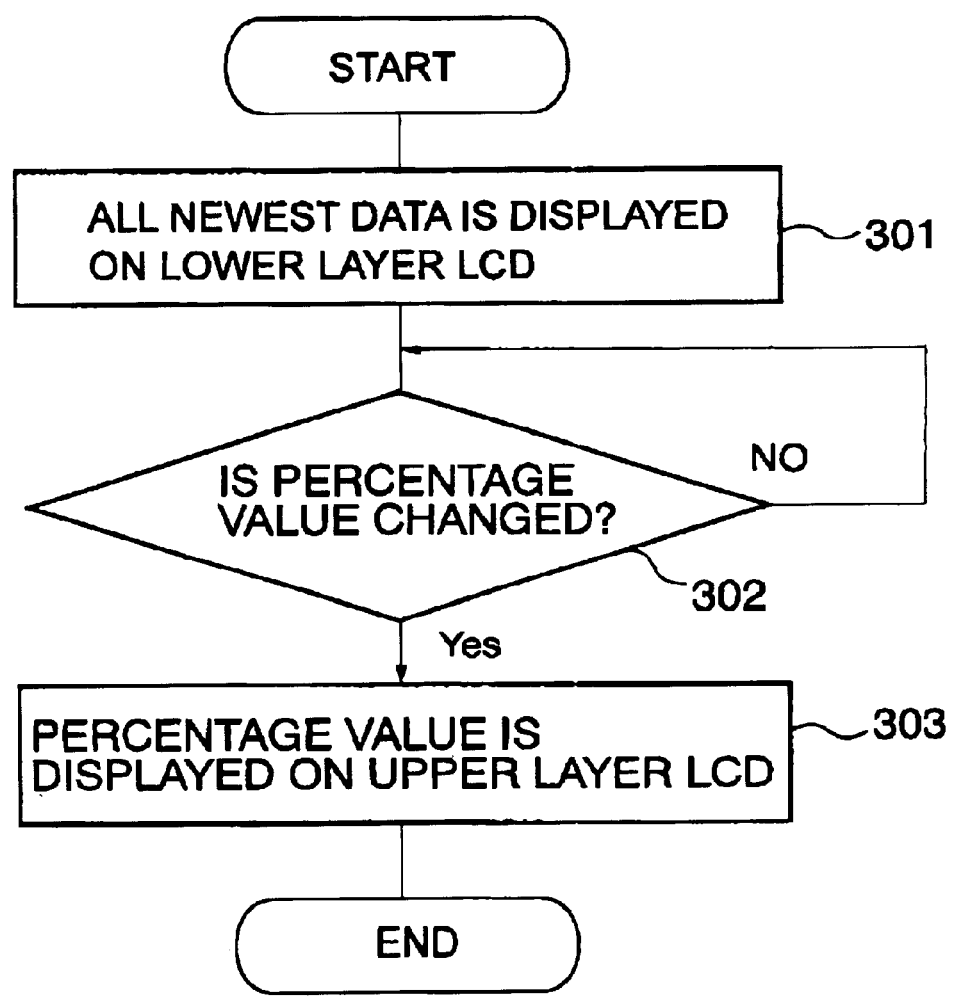
FIG. 13 is a flowchart showing an operation for changing a screen over to another screen due to a change in ratio of a physical quantity to a target value of the physical quantity in the measurement device according to the embodiment mode of the present invention.

FIG. 13 is a flowchart showing an operation for changing a screen over to another screen due to a change in a ratio of the physical quantity to the target value in the measurement device according to this embodiment mode. Referring now to FIG. 13, the measurement device 10 previously displays the newest data of all the items on the lower surface display unit 17 (Step 301). The measurement device 16 monitors a change in a ratio of the physical quantity to the target value (% value) (Step 302). If there is a change, then the measurement unit 10 displays the newest data of the ratio on the upper surface display unit 16 (Step 303).

Figure 14:
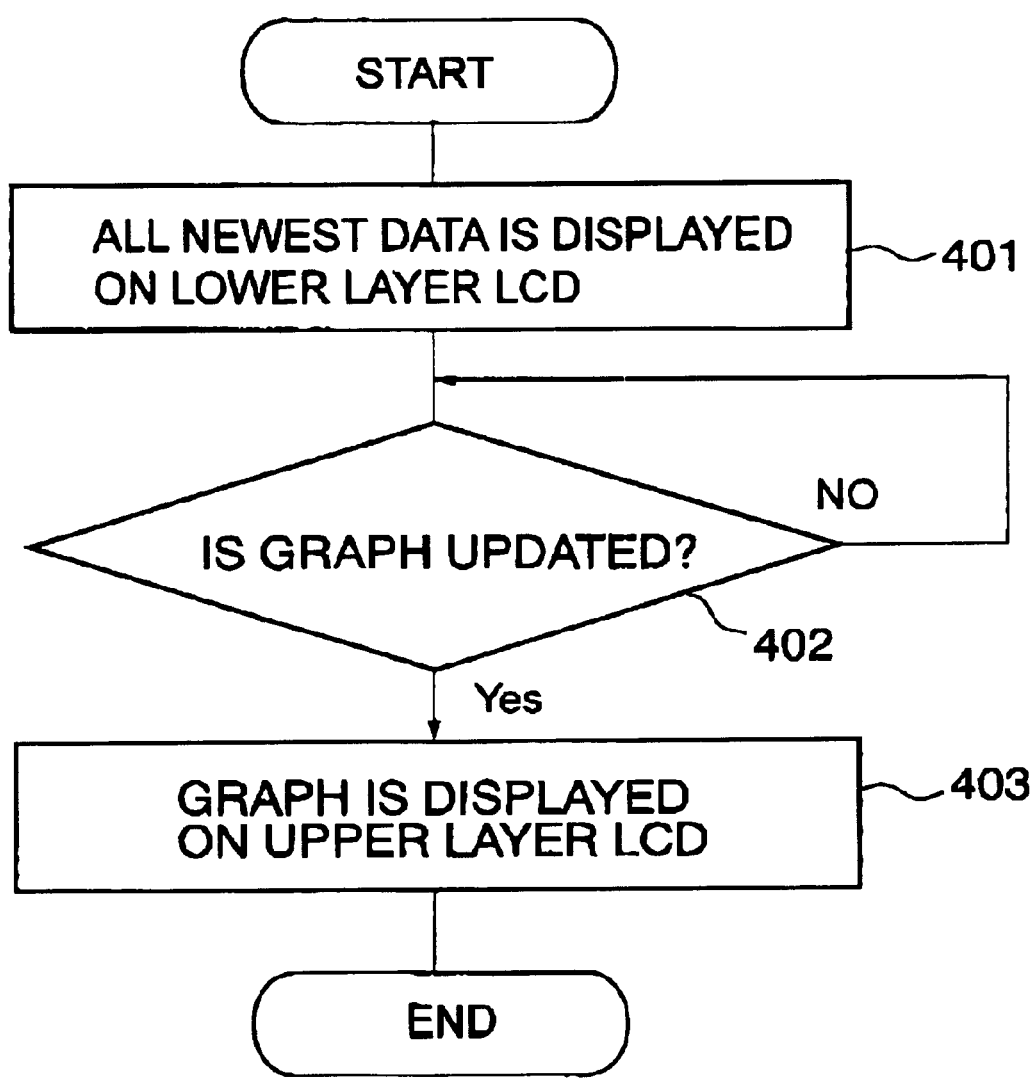
FIG. 14 is a flowchart showing an operation for changing a screen over to another screen due to update of a graph representing a change in physical quantity in the measurement device according to the embodiment mode of the present invention.

FIG. 14 is a flowchart showing an operation for changing a screen over to another screen through updating the graph representative of a change in physical quantity in the measurement device according to this embodiment mode. Referring now to FIG. 14, the measurement device 10 previously displays the newest data of all the items on the lower surface display unit 17 (Step 401) The measurement device 10 periodically updates the graph and monitors the update, for example (Step 402). If the updating operation is confirmed, then the measurement unit 10 displays the updated graph on the upper surface display unit 16 (Step 403).

Figure 15:
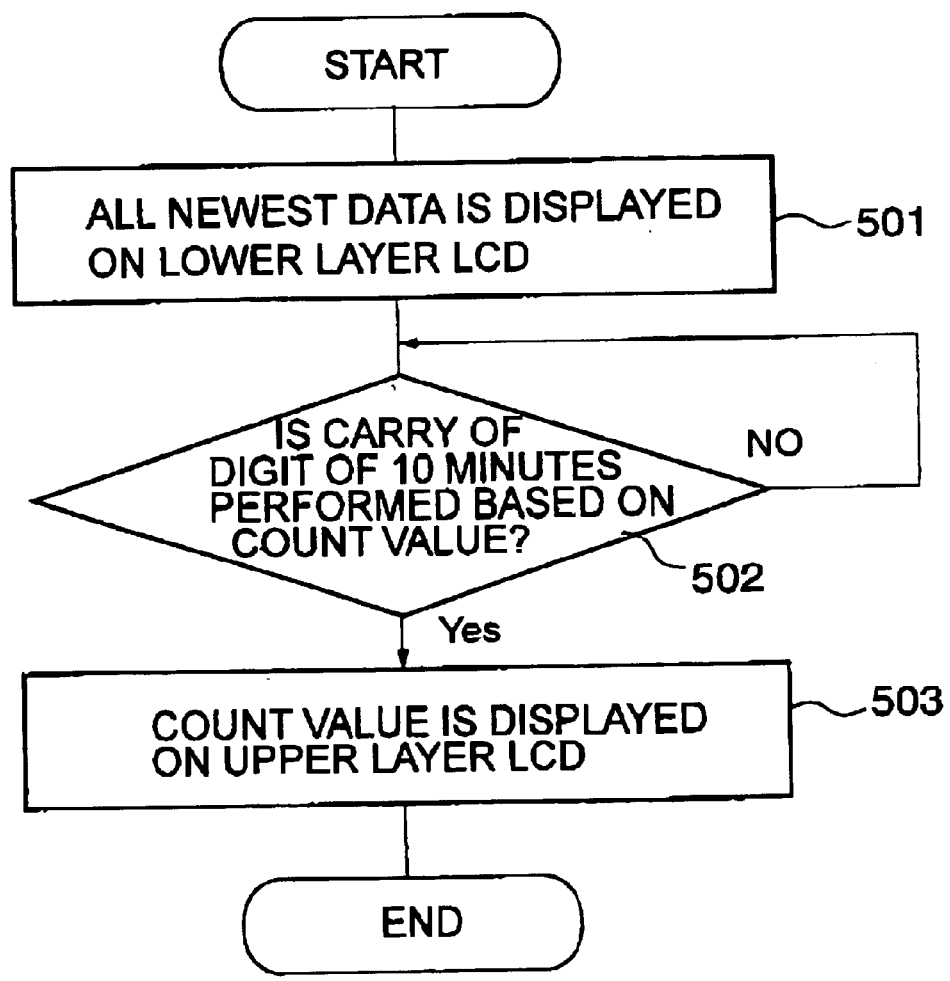
FIG. 15 is a flowchart showing an operation for changing a screen over to another screen due to a lapse of a predetermined time in the measurement device according to the embodiment mode of the present invention.

FIG. 15 is a flowchart showing an operation for changing a screen over to another screen due to a lapse of a predetermined period of time in the measurement device according to this embodiment mode. Referring now to FIG. 15, the measurement device 10 previously displays the newest data of all the items on the lower surface display unit 17 (Step 501). The measurement device 10 usually monitors a lapse of a predetermined period of time (Step 502). For example, the measurement device 10 usually monitors a carry of a digit of 10 minutes to thereby monitor a lapse of 10 minutes. After a lapse of the predetermined period of time, the measurement device 10 displays the newest data of a count value on the upper surface display unit 16 (Step 503).

Figure 16:
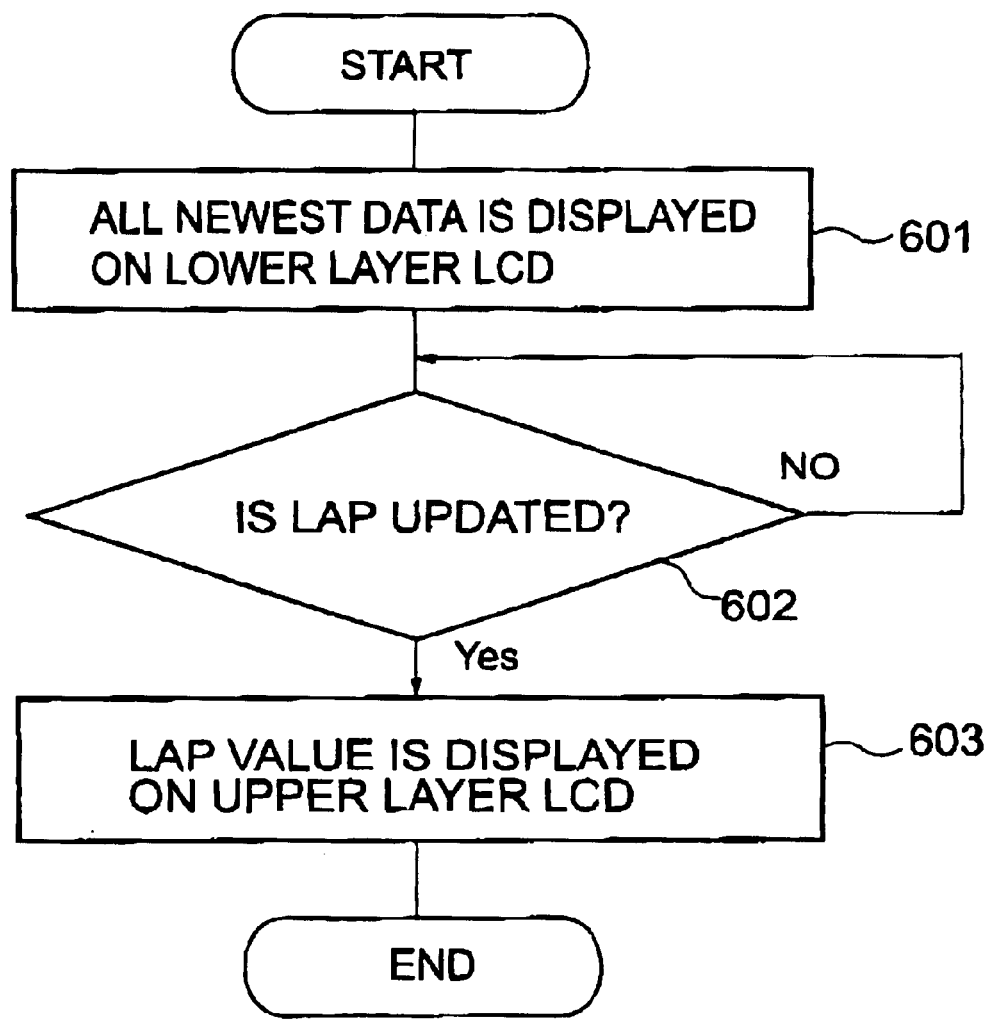
FIG. 16 is a flowchart showing an operation for changing a screen over to another screen due to update of a lap in the measurement device according to the embodiment mode of the present invention.

FIG. 16 is a flowchart showing an operation for changing a screen over to another screen through updating the lap in the measurement device according to this embodiment mode. Referring now to FIG. 16, the measurement device 10 previously displays the newest data of all the items on the lower surface display unit 17 (Step 601). The measurement device 10 monitors the update of the lap (Step 502). If the updating operation is confirmed, then the measurement unit 10 displays the newest data of the lap value on the upper surface display unit 13 (Step 603).

In addition, according to the measurement device 10 of this embodiment mode, a plurality of kinds of data are displayed on the lower surface display unit 17, and if any of the data is selected by the user, then the data concerned is magnified and displayed on the upper surface display unit 16. As a result, a plurality of kinds of data can be checked by the user, and the data which the user demands to check can be readily checked.

In addition, according to the measurement device 10 of this embodiment mode, a plurality of kinds of data are displayed on the lower surface display unit 17, and if any of the data is updated, then the data concerned is automatically magnified and displayed on the upper surface display unit 16. As a result, a plurality of kinds of data can be checked by a user, and the data involving a change can be readily checked.

In addition, according to the measurement device 10 of this embodiment mode, since the ratio of the measured physical quantity to the target value of the physical value is displayed, it is possible to readily grasp a relationship between the measured physical quantity and the target value of the physical value.

Note that, while in this embodiment mode, any one of items is displayed on the upper surface display unit 16, the present invention is not intended to be limited to such a case. That is to say, at least one item selected from the items displayed on the lower surface display unit 17 has to be magnified and displayed so as to be readily visually recognized.

According to the measurement device of the present invention, the data of a plurality of items is displayed on the first display means, and any of the data is magnified and displayed on the first display means. As a result, a plurality of kinds of data can be checked, and also the data of the specific item can be readily checked.

In addition, the data of a plurality of items is displayed on the second display means, and the data of the items meeting the predetermined conditions is automatically magnified and displayed on the first display means. As a result, a plurality of kinds of data can be checked, and the data involving a change can be readily checked as well.

In addition, the data of a plurality of items is displayed on the second display means, and the data of the items selected by a user is magnified and displayed on the first display means. As a result, the data of a plurality of items can be checked, and also the data which a user demands to check can be readily checked.

Also, since the ratio of the measured physical quantity to the target value of the physical quantity is displayed, it is possible to readily grasp a relationship between the measured physical quantity and the target value.

Also, the data of a plurality of items displayed on the second display means can be visually recognized, and the data magnified and displayed on the first display means can be readily visually recognized as well.

What is claimed is:

1. A measurement device, comprising:
   physical quantity measurement means for measuring a physical quantity;
   time measurement means for counting an elapsed time;
   calculating means for receiving the physical quantity measured by the physical quantity measurement means and the elapsed time counted by the time measurement means and calculating a plurality of items;
   first display means for simultaneously displaying thereon the plurality of items; and
   second display means for displaying at least one of the plurality of items in an enlarged manner relative to the first display means.

2. A measurement device according to claim 1; further comprising display control means for controlling the second display means to display a selected item in an enlarged manner when any one of the items meets a predetermined condition.

3. A measurement device according to claim 2; wherein the display control means controls the second display means to display the selected item in an enlarged manner when any one of the items is updated.

4. A measurement device according to claim 1; further comprising switch input means for selecting any one of the items based on user manipulation of a switch; and display control means for controlling the second display to display the selected item in an enlarged manner.

5. A measurement device according to claim 1; wherein the physical quantity comprises at least one of a heart rate, a pulse rate, an atmospheric pressure, and an atmospheric temperature.

6. A measurement device according to claim 5; wherein the items comprise at least a ratio of a physical quantity to a preset target value.

7. A measurement device according to claim 1; wherein the items comprise at least a ratio of a physical quantity to a preset target value.

8. A measurement device according to claim 1; wherein the second display means is semitransmissive, and the first display means and the second display means overlap each other such that a display appearing on the first display means is transmitted through the second display means to be visually recognized.

9. A measurement device according to claim 1; wherein the measurement device is a wrist-wearable measurement device.

10. A data displaying method which is used for a measurement device having first display means for simultaneously displaying thereon a plurality of items that are determined based on a measured physical quantity, and second display means for displaying any one of the items in an enlarged manner relative to the first display means, the method comprising:
    a step of continuously displaying the plurality of items on the first display means; and
    a step of displaying one of the plurality of items on the second display means in an enlarged manner relative to the first display means when the item satisfies a predetermined condition.

11. A data displaying method which is used for a measurement device having first display means for simultaneously displaying thereon a plurality of items that are determined based on a measured physical quantity, and second display means for displaying any one of the items in an enlarged manner relative to the first display means, the method comprising:
    a step of continuously displaying the plurality of items on the first display means; and
    a step of displaying one of the plurality of items on the second display means in an enlarged manner relative to the first display means in response to a switch input.

12. A measurement device, comprising:
    a physical quantity measurement circuit for measuring a physical quantity;
    a time measurement circuit for counting an elapsed time;
    a calculating circuit for receiving the physical quantity measured by the physical quantity measurement circuit and the time counted by the time measurement circuit and calculating a plurality of items;
    a first display for simultaneously displaying the plurality of items; and
    a second display for displaying at least one of the plurality of items in an enlarged manner relative to the first display.

13. A measurement device according to claim 12; further comprising a display control circuit for controlling the second display to display a selected item in an enlarged manner when any one of the items meets a predetermined condition.

14. A measurement device according to claim 13; wherein the display control circuit controls the second display to display the selected item in an enlarged manner when any one of the items is updated.

15. A measurement device according to claim 14; further comprising a manually-operable switch for selecting any one of the items.

16. A measurement device according to claim 12; wherein the physical quantity comprises at least one of a heart rate, a pulse rate, an atmospheric pressure, and an atmospheric temperature.

17. A measurement device according to claim 12; wherein the items comprise at least a ratio of a physical quantity to a preset target value.

18. A measurement device according to claim 12; wherein the second display is semitransmissive, and the first display and the second display overlap each other such that a display appearing on the first display is transmitted through the second display to be visually recognized.

* * * * *